US007202219B1

(12) United States Patent
Vigh et al.

(10) Patent No.: US 7,202,219 B1
(45) Date of Patent: Apr. 10, 2007

(54) USE OF D-TAGATOSE AS A PREBIOTIC FOOD COMPONENT (75) Inventors: Mads Liendgaard Vigh, Viby J. (DK); Henrik Andersen, Viby J. (DK)

(73) Assignee: MD Foods AMBA, Viby J. (DK)

( * ) Notice: Subject to any disclaimer, the term of this patent is extended or adjusted under 35 U.S.C. 154(b) by 973 days.

(21) Appl. No.: 09/255,655

(22) Filed: Feb. 23, 1999

Related U.S. Application Data (60) Provisional application No. 60/075,694, filed on Feb. 24, 1998.

(51) Int. Cl.
*A61K 31/70* (2006.01)
*C07H 1/00* (2006.01)
*A01N 63/00* (2006.01)
*C12N 1/20* (2006.01)

(52) U.S. Cl. .................... 514/23; 514/25; 536/1.1; 536/125; 424/93.45; 435/252.9

(58) Field of Classification Search ................ 514/23, 514/25; 536/1.1, 125; 424/93.45; 435/252.9
See application file for complete search history.

(56) References Cited

U.S. PATENT DOCUMENTS

| 4,786,722 | A | * | 11/1988 | Zehner ................ 536/1.1 |
| 5,002,612 | A | | 3/1991 | Beadle et al. ............ 127/46.1 |
| 5,078,796 | A | | 1/1992 | Beadle et al. ............ 127/46.1 |
| 5,356,879 | A | | 10/1994 | Zehner et al. ............. 514/25 |
| 5,447,917 | A | * | 9/1995 | Zehner et al. ............. 514/23 |
| 5,468,734 | A | | 11/1995 | Seri et al. |
| 5,709,857 | A | * | 1/1998 | Morelli et al. ........... 424/93.45 |

FOREIGN PATENT DOCUMENTS

| EP | 0 560 284 B1 | 7/1997 |
| JP | 06-065080 | 3/1994 |

OTHER PUBLICATIONS

Mortensen, Per Brobech et al., "Short Chain Fatty Acid Production . . . ", American Institute of Nutrition, pp. 321-325, 1987.*
Macfarlane, G.T. et al., "The Colonic Flora . . . " Physiology, Pathophysiology and disease, pp. 51-92, 1991.*
Daly, Charles et al., "Technological and Health Benefits of Dairy Starter Cultures," *Int. Dairy Journal*, vol. 8, pp. 195-205 (1998).
Fardet, Anthony et al., "In Vitro Fermentation of Beet Fibre and Barley Bran, of their Insoluble Residus after Digestion and Ileal Effluents," *J. Sci. Food Agric.*, vol. 75, pp. 315-325 (1997).

(Continued)

*Primary Examiner*—Shaojia Anna Jiang
*Assistant Examiner*—Everett White
(74) *Attorney, Agent, or Firm*—Finnegan, Henderson, Farabow, Garrett, & Dunner, L.L.P.

(57) ABSTRACT

Oral intake of D-tagatose in a prebiotic food induces production of butyrate and stimulates the growth of beneficial bacteria in the human colon. Therefore it is believed to be useful in food or the like as preventive drug against colon cancer.

10 Claims, 5 Drawing Sheets

OTHER PUBLICATIONS

Hague, A. et al., "The Short-Chain Fatty Acid Butyrate Induces Apoptosis in Colorectal Tumor Cell Lines," *European Journal of Cancer Prevention*, vol. 4, pp. 359-364 (1995).

Hague, Angela et al., "The Role of Butyrate in Human Colonic Epithelial Cells: An Energy Source or Inducer of Differentiation and Apoptosis?," *Proceedings of the Nutrition Society*, vol. 55, pp. 937-943 (1996).

Johnson, I.T., "Butyrate and Markers of Neoplastic Change in the Colon," *European Journal of Cancer Prevention*, vol. 4, pp. 365-371 (1995).

Klaenhammer, Todd R., "Functional Activities of *Lactobacillus* Probiotics: Genetic Mandate," *Int. Dairy Journal*, vol. 8, pp. 497-505 (1998).

Macfarlane, G.T. et al., The Colonic Flora, Fermentation, and Large Bowel Digestive Function; in The Large Intestine, *Physiology, Pathophysiology and Disease*, Chapter 4, pp. 51-92 (1991).

Martin, Lucile J.M. et al., "Production of Short-Chain Fatty Acids from Resistant Starch in a Pig Model," *J. Sci. Food Agric.*, vol. 77, pp. 71-80 (1998).

Mortensen, Per Brobech et al., "Short-Chain Fatty Acid Production from Mono- and Disaccharides in a Fecal Incubation System: Implications for Colonic Fermentation of Dietary Fiber in Humans," *American Institute of Nutrition*, pp. 321-325 (1987).

Rapaille, A. et al., "Maltitol, recent findings on colonic health," Fie Seminars, pp. 124-127 (1997).

Roediger, W.E.W., "Role of Anaerobic Bacteria in the Matabolic Welfare of the Colonic Mucosa in Man," *Gut*, vol. 21, pp. 793-798 (1980).

Velázquez, Omaida C. et al., "Butyrate and the Colonocyte: Implications for Neoplasia," *Digestive Diseases and Sciences*, vol. 41, No. 4, pp. 727-739 (1996).

\* cited by examiner

USE OF D-TAGATOSE AS A PREBIOTIC FOOD COMPONENT

This application claims the benefit of provisional application No. 60/075,694, filed Feb. 24, 1998.

BACKGROUND OF THE INVENTION

1. Field of the Invention

This invention relates to the use of D-tagatose as a prebiotic component. It can be used as a prebiotic food, food additive or food supplement.

Tests have surprisingly shown that oral intake of the unabsorbable carbohydrate, D-tagatose, induces production of butyrate in colon. From the literature it is known that butyrate possibly has a colon cancer protective effect. Further, tests have shown that oral intake of D-tagatose stimulates the growth of beneficial lactobacilli and lactic acid bacteria in the human colon. Therefore, D-tagatose is useful as a prebiotic food to stimulate the growth of beneficial bacteria and to induce the production of butyrate. Such prebiotic food is thus presumably useful for normalizing the bacterial flora in the colon and for preventing the risk of colon cancer in human beings.

D-tagatose is a well-known keto-hexose which is useful as a reduced-calorie food sweetening and bulking agent, and as an additive in detergent, cosmetic and pharmaceutical formulations. U.S. Pat. Nos. 5,002,612 and 5,078,796 to Beeadle et al. teach processes of making D-tagatose by isomerizing a mixture containing D-galactose with a metal hydroxide in the presence of a catalyst at a relatively low temperature to form an intermediate complex, followed by neutralization with acid to yield D-tagatose.

D-tagatose is known as an anti-hyperglycaemic agent that can be used to inhibit formation of advanced glycosylation in products in mammals, as described in U.S. Pat. Nos. 5,356,879 and 5,447,917 to Zehner et al. D-tagatose also is known as a low-calorie carbohydrate sweetener and bulking agent that can be used in the preparation of sweetened edible formulations in stead of sucrose, as taught in U.S. Pat. No. 4,786,722 to Zehner.

2. Description of the Related Art

The mucosal surfaces of the intestinal tract are amongst the main sites of cell replication in the human body. In the colon the epithelial cells are exposed not only to the circulation and to the endogenous secretions of other mucosal cells, but also to the contents of the colonic lumen which is rich in food residues and the metabolic products of the micro flora. (I. T. Johnson "Butyrate and markers of neoplastic change in the colon", European Journal of Cancer Prevention, Vol. 4, 1995) Epidemiological and animal studies suggest that dietary fat and protein may promote carcinogenesis in the colon, whereas increases in fibre and complex carbohydrates in the diet may protect against colon cancer. Colonic luminal butyrate concentrations are postulated to be the key protective component of high-fibre diets against colon cancer (O. C. Velázquez, H. W. Lederer and J. L. Rombeau 1996. "Butyrate and the Colonocyte: Implications for Neoplasia", Digestive Diseases and Science Vol. 41, No. 4: 727–739).

Butyrate is one of the short-chain fatty acids (SCFA), i.e. the C2–5 organic acids. These compounds are formed in the gastrointestinal tract of mammals as a result of anaerobic bacterial fermentation of undigested dietary components, and are readily absorbed by the colonic epithelium. Dietary fibre is the principal substrate for the fermentation of SCFA in humans, however, intake of fibres is often low in a typical western diet. Other undigested components, like starch, proteins, contribute to the production of SCFA, but also low-molecular weight oligosaccharides, sugars, and polyols, which escape digestion and absorption in the small intestine, contribute to the production of SCFA. In the mammalian hind gut, acetate, propionate, and butyrate account for at least 83% of SCFA and are present in a nearly constant molar ratio 60:25:15 (Velazquez et al., supra).

In vitro studies on fibre and other indigestible carbohydrates in human faecal incubations indicate 3–22% butyrate, only various forms of starches and resistant starches had a butyrate proportion of 22–29% (F. Bornet, C. Alamowitch and G. Slama 1994. "Acides Gras Volatils: Des actions sur le metabolisme glucidique", Rev Prat 44(8):1051–1055). Similarly, ileal effluents from pigs eating beet fibre and barley bran incubated in human faecal slurry in vitro incubation did not increase the proportion of butyrate beyond the 18% observed with ileal effluents from a fibre free pig diet (A. Fardet, F. Guillon, C. Hoebler and J-L. Barry 1997. "In vitro fermentation of beet fibre and barley bran, of their insoluble residues after digestion and ileal effluents", J. Sci Food Agric 75: 315–325). In a pig study ingesting either raw potato starch, hylon starch or retrograded hylon starch, the molar proportion of butyrate was not higher than 14% at the highest level, which was in the proximal colon, and similarly the in vitro incubation showed only between 14 and 25% butyrate (mol %) (L. J. M. Martin, H. J. W. Dumon and M. M. J. Champ 1998. "Production of short-chain fatty acids from resistant starch in a pig model", J. Sci. Food Agric. 77:71–80.

A study of fermentation of mono- and disaccharide in a human faecal in vitro system, indicated a high proportion of butyrate on fermentation of sorbitol, galacturonic acid and glucoronic acid (P. B. Mortensen, K. Holtug and H. S. Rasmussen 1988, "Short-chain fatty acid production from mono- and disaccharides in a faecal incubation system: Implications for colonic fermentation of dietary fiber in humans", J. Nutr. 118:321–325). The findings of high butyrate with sorbitol are not confirmed on incubation with maltitol, which consists of 50% glucose and 50% sorbitol, as in vitro incubation of maltitol only indicated 10% butyrate (A. Rapaille and F. Bornet, "Maltitol, recent findings on colonic health", FIE London 1997).

The colonic epithelium is a dynamic tissue in a state of continual renewal. Cells proliferate in the lower two-thirds of the normal colonic crypt, and cease dividing as they migrate further up the crypt. The continuous movement of cells up the colonic crypt is tightly linked to differentiation (A. Hague, A. J. Butt and C. Paraskeva 1996 "The role of butyrate in human colonic epithelial cells: An energy source or inducer of differentiation and apoptosis", Proceedings of the Nutrition Society 55:937–943).

Butyrate appears to be of central importance to the colonic epithelium because it is the major and preferred fuel (W. E. W. Roediger 1980, "Role of anaerobic bacteria in the metabolic welfare of the colonic mucosa in man", Gut 21:793–798) and plays a role in the control of proliferation and differentiation of colonic epithelial cells. Many studies have demonstrated that butyrate is trophic to the colonic mucosa at physiological concentrations, and this is due to an acceleration of crypt cell proliferation (Johnson, supra).

In many tissues undergoing rapid turnover of cells, apoptosis is involved in the maintenance of tissue homeostasis. In the gut, where the epithelial cells are exposed to dietary carcinogens, cells undergo apoptosis as a means of eliminating damaged cells and, thus, protecting the tissue against neoplastic changes. Several in vitro studies have indicated that butyrate causes apoptosis at physiological concentrations (2–4 mM) (A. Hague and C. Paraskeva "The short-chain fatty acid butyrate induces apoptosis in colorectal tumor cell lines", European Journal of Cancer Prevention, Vol. 4, 1995).

In contrast to the above mentioned trophic effect of butyrate on normal mucosa, the growth of neoplastic colonocytes is arrested by butyrate, which also inhibits the preneoplastic hyper proliferation induced by tumor promotor in vitro. The uncontrolled growth of cancer cell lines is stopped, and differentiation is induced by butyrate (Velazquez et al., supra).

The lactobacilli are important inhabitants of the intestinal tract of man and animals. *Lactobacillus* species, notably *Lactobacillus acidophilus*, are most often implicated in assisting the establishment of a 'normal micro flora', especially following antibiotic therapy. In addition, probiotic lactobacilli have been implicated in a variety of beneficial roles, including (T. R. Klaenhammer 1998, "Functional activities of *lactobacillus* probiotics: Genetic mandate", Int. Dairy Journal 8:497–505): Maintenance of the normal micro flora, pathogen interference, exclusion and antagonism, immunostimulation and immunomodulation, anticarcinogenic and antimutagenic activities, deconjugation of bile acids, lactase presentation in vivo.

Another effect mentioned of *lactobacillus* is reduction in blood cholesterol (C. Daly, G. F. Fitzgerald, L. O'Conner and R. Davis 1998, "Technological and health benefits of dairy starter cultures", Int. Dairy Journal 8:195–205)

A lot of studies on probiotic bacteria have shown that it is very difficult for these bacteria to colonize the human colon, that is after having stopped supply of probiotic bacteria in the diet, they disappear from faeces. This makes it more obvious to isolate possible probiotic bacteria from the human intestine (U.S. Pat. No. 5,709,857). It is even more obvious to selectively feed the *lactobacillus* already present in the colon (prebiotic concept).

The literature on beneficial effects and mechanism on both butyrate and *lactobacillus* is very abundant, so only recent review type articles are referred to in this section.

SUMMARY OF THE INVENTION

D-tagatose is a naturally-occurring keto-hexose which only differs from D-fructose at the fourth carbon atom. The rather small difference has big implications on the overall metabolism of D-tagatose, as only 15–20% of ingested D-tagatose is absorbed in the small intestine. The major part of ingested D-tagatose is fermented in the colon by indigenous micro flora resulting in production of short-chain fatty acids (SCFA). The novelty of D-tagatose is that the fermentation induces a very unique profile of SCFA's with a high proportion of butyrate. These findings are documented in in vitro and in vivo studies in pig and in human faecal in vitro experiments.

Human studies document that generally accepted beneficial bacteria, like lactobacilli and lactic acid bacteria, are increased in human faeces upon ingestion of D-tagatose.

Being a potential future food ingredient with a sweetness similar to sucrose, D-tagatose is an ideal ingredient for application in a range of food products. The ideal fermentation products of D-tagatose with a high proportion of butyrate and stimulation of growth of lactobacilli make D-tagatose an ideal future prebiotic food ingredient that keeps a healthy balance in the colon and may have even a cancer protective role.

Thus, the invention relates to use of D-tagatose as a prebiotic food, food additive or food supplement.

D-tagatose has been shown to induce production of butyrate by bacteria in the human colon and to stimulate growth of lactobacilli and lactic acid bacteria in the human colon. This makes D-tagatose a possible candidate for the production of a drug for preventing colon cancer.

D-tagatose can be taken orally in an effective amount to induce production of butyrate in the human colon and/or to stimulate the growth of lactobacilli and lactic bacteria in the human colon. Such amount will normally be 5 to 30 gram, and preferably 5 to 15 gram a day taken 1–3 times a day. D-tagatose can be taken in any normal food product, such as confectionery, chewing gum, ice cream, dessert, soft drink, breakfast cereal, yoghurt, health drink or health bar. It has been proposed to substitute sucrose or to sweeten such products using D-tagatose. It is of course also possible to use D-tagatose as such, for example as a sweetener in coffee, tea or the like, or to take it as it is or in a formulated form, such as tablets. The amounts effective to achieve the useful effects according to the invention are the same as normally used to sweeten food products and/or to give them the normal bulk effect.

This is achieved by incorporation of 10–20% by weights of D-tagatose in breakfast cereals, where the normal serving is 60 g, 5–10% by weight of D-tagatose in breakfast yoghurt, where the normal serving is 150 g. Further, it is proposed to incorporate 2–4% by weight in health drinks, where the normal serving is 250–330 ml and 20–30% by weight in health bars, where the normal serving is 30 to 50 g.

The accompanying drawing illustrates the invention.

DETAILED DESCRIPTION OF THE INVENTION

The invention is further illustrated by the following non-limiting examples.

Example 1

In the study, one group of 8 pigs was having a standard diet+15% sucrose (unadapted), and another group of 8 pigs was fed a standard diet+5% sucrose+10% D-tagatose (adapted) for 17 days.

On the 17. day the pigs were killed 3 hours after the morning feeding, and the entire gastrointestinal tract was sectioned. Content from mid-colon was used for in vitro fermentation assays. 20% slurries were incubated at 37° C. and anaerobic conditions for 4 hours with or without 1% D-tagatose added. The amount of SCFA produced by D-tagatose is calculated as the amount produced in the assay with 1% D-tagatose added subtracted by the amount produced in the assay without D-tagatose.

Table 1 shows that colon content from adapted pigs ferments D-tagatose in a very special way with low acetate and high butyrate and valerate, whereas the colon content from unadapted pigs gives a rather normal SCFA profile with less than 20% butyrate and a high proportion of acetate. The overall fermentation rate, measured as rate of degradation of D-tagatose, is low in in vitro incubation with D-tagatose in unadapted pigs, 1.1 g of D-tagatose pr hour pr kg digesta versus 15.3 g of D-tagatose pr hour pr kg digesta in adapted pigs.

TABLE 1

In vitro Incubations - 3 Hours after Slaughtering
Mole % of SCFA after microbial fermentation of D-Tagatose

|  | Control pigs | | D-tagatose pigs | |
| --- | --- | --- | --- | --- |
|  | caecum | colon | caecum | colon |
| Formate | 2.5 | 0.0 | 14.4 | 3.7 |
| Acetate | 54.8 | 70.1 | 21.5 | 23.3 |
| Propionate | 11.2 | 0.0 | 17.0 | 4.0 |
| Butyrate | 18.2 | 16.7 | 21.8 | 46.3 |
| Valerate | 11.1 | 7.8 | 23.4 | 15.1 |
| Capronate | 2.0 | 4.8 | 1.9 | 6.8 |
| Heptanoate | 0.2 | 0.6 | 0.0 | 0.8 |
| Total | 100.0 | 100.0 | 100.0 | 100.0 |
| Tagatose degradation g/h/kg digesta | 2.7 | 1.1 | 3.7 | 15.3 |

Production (0–4 h) of SCFA = SCFA (1% tagatose added) – SCFA (no tagatose added)

Example 2

In this study, 3 groups of each 2 pigs were having a standard pig diet+20% sucrose, a standard pig diet+10% sucrose+10% D-tagatose, and a standard pig diet+20% D-tagatose for 33 days. The pigs were killed on the 33. day 6 hours after morning feeding, and the entire gastrointestinal tract was divided into 8 segments.

The concentrations of the various SCFA were measured in the 8 sections immediately after killing, and further the content from the 8 sections was used for 12 hour in vitro incubations at 37° C. and anaerobic conditions. In this in vitro assay no D-tagatose was added, and the fermentation products originate from unabsorbed D-tagatose and other undigestible food components from the diets.

Figure 1:
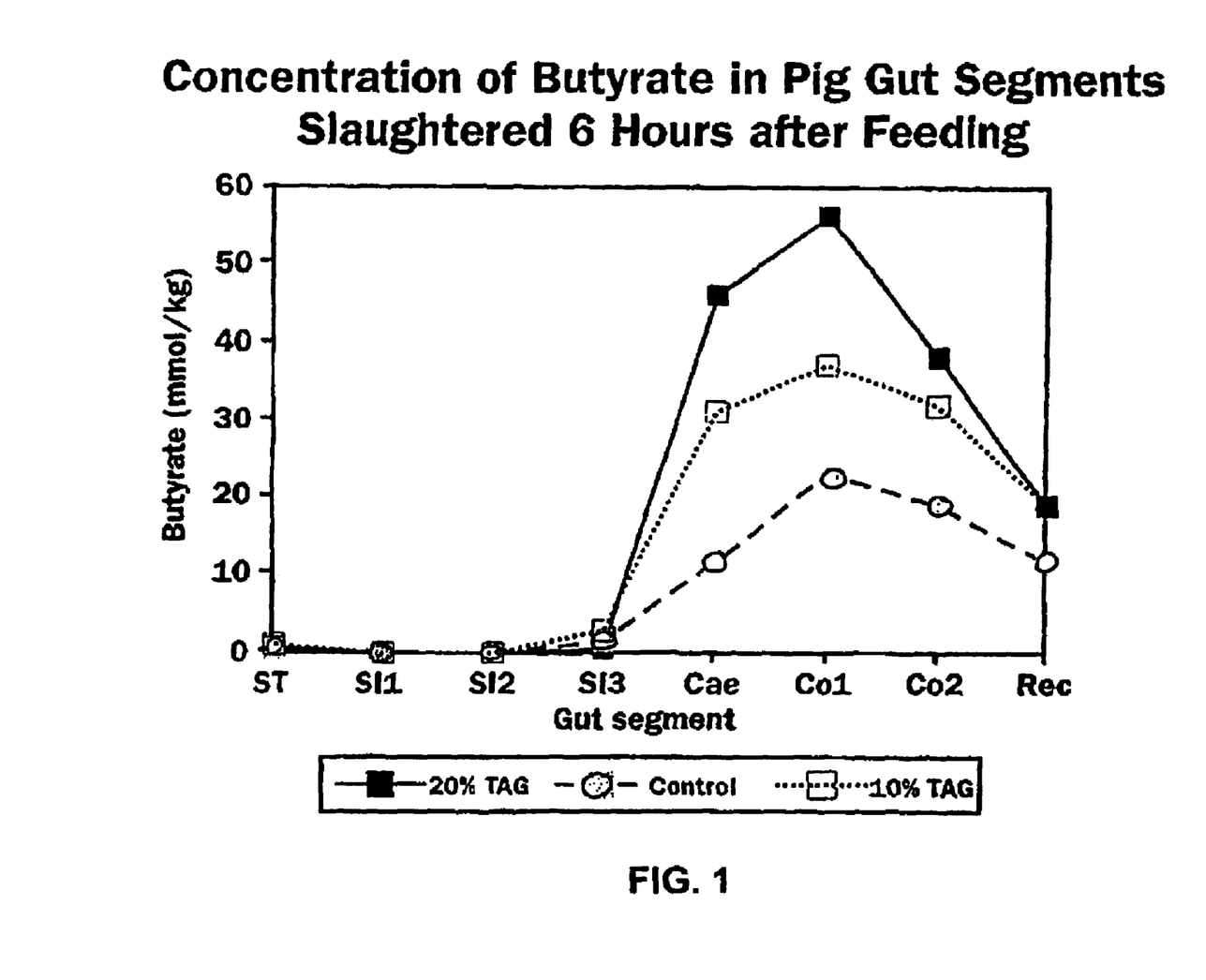
FIG. 1 shows the concentration of butyrate in various gastrointestinal sections.

FIG. 1 shows the concentration of butyrate in the various gastrointestinal sections at the time of slaughtering. The results clearly indicate that butyrate is present only in the hind gut, as expected, and that butyrate is increasing in a dose response manner to the intake of D-tagatose.

Figure 2:
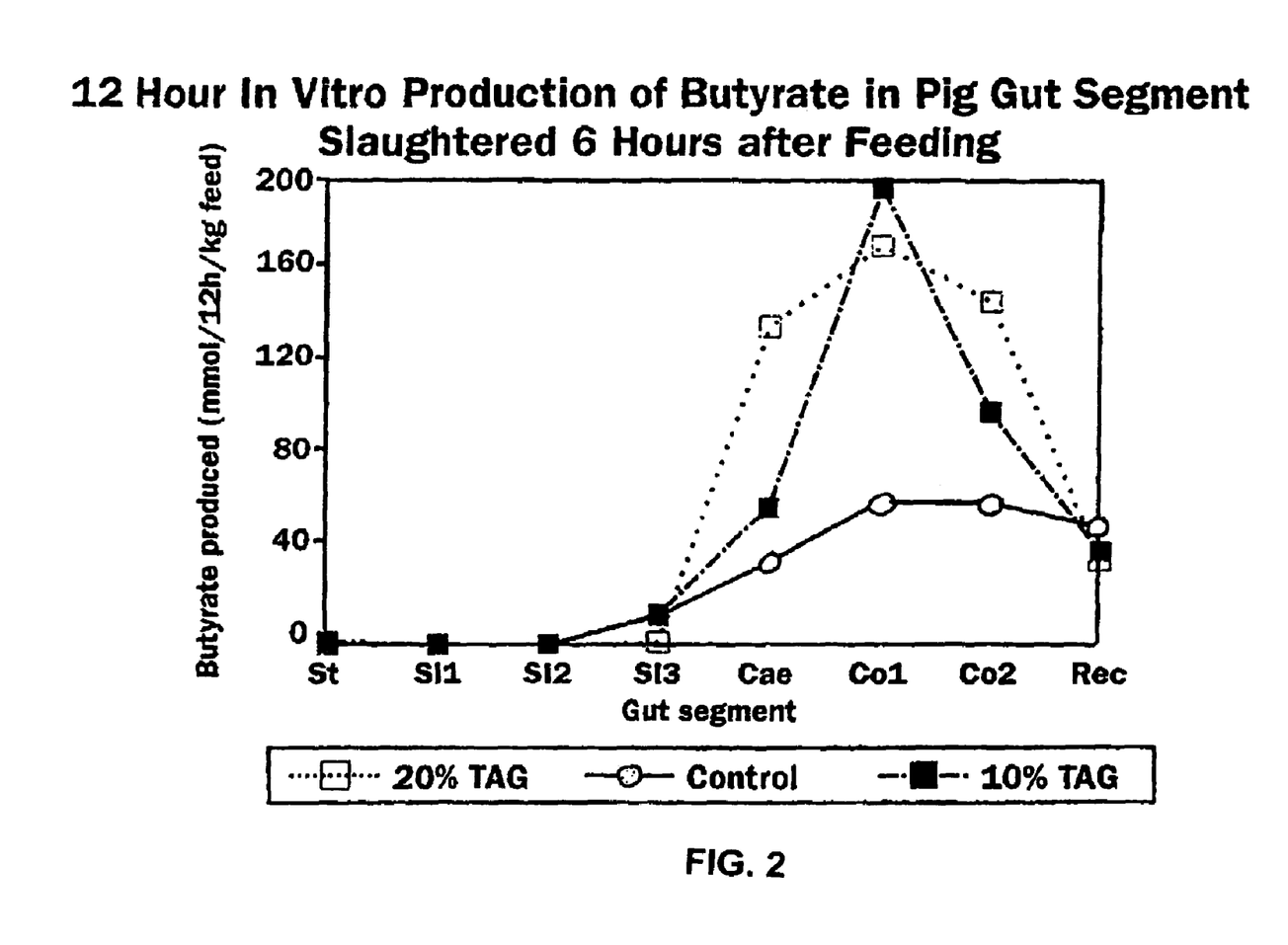
FIG. 2 shows the 12 hour in vitro production of butyrate in the content from different gut sections.

FIG. 2 shows that the 12 hour in vitro production of butyrate similarly is acting in a dose response manner to the intake of D-tagatose in the diet.

The following abbreviations are used in FIGS. 1 and 2:

st=stomach

SI1=small intestine section 1

SI2=small intestine section 2

SI3=small intestine section 3

Cae=caecum

Co1=colon section 1

Co2=colon section 2

Rec 0 rectum

Figure 3:
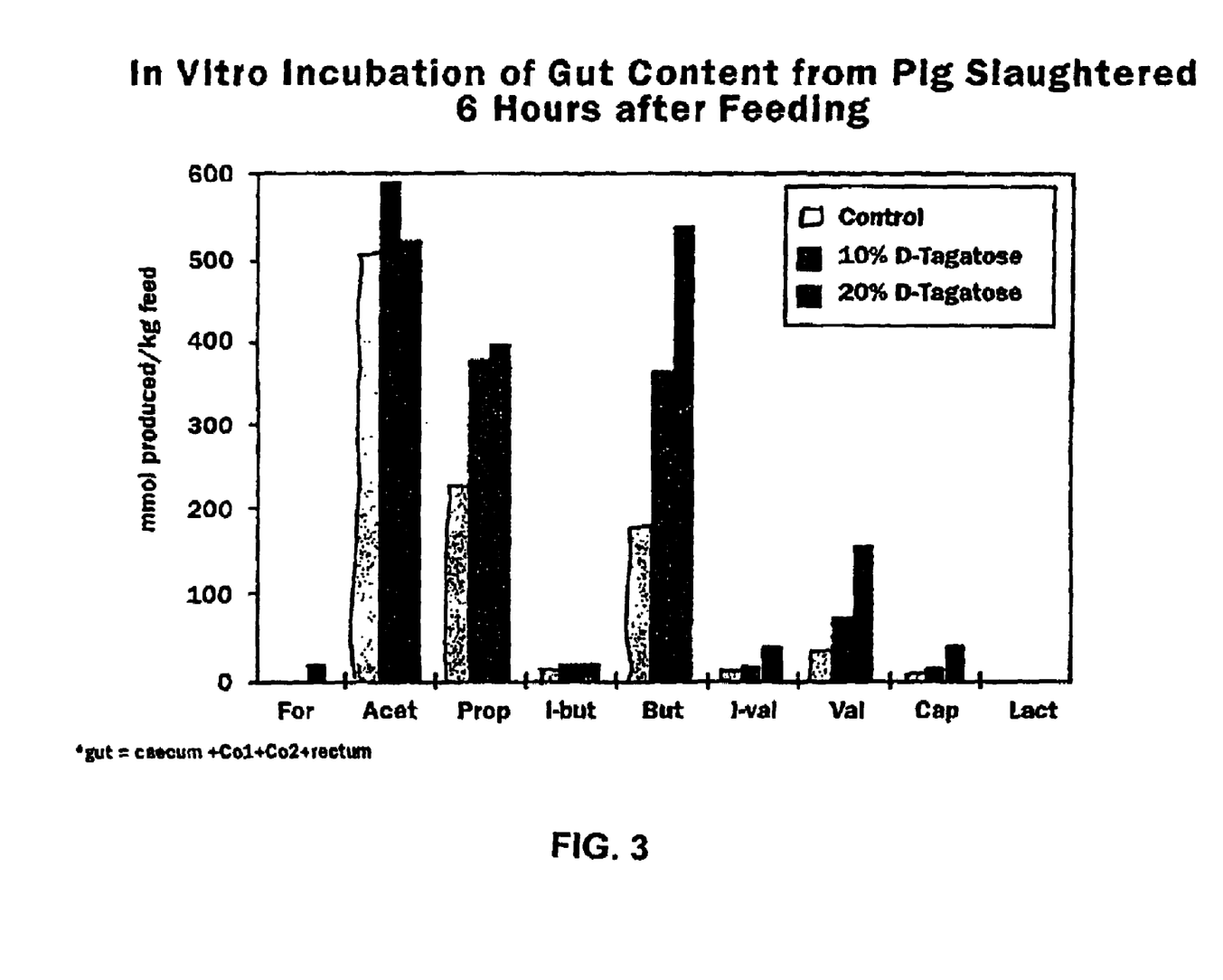
FIG. 3 shows the total 12 hour in vitro production of SCFA.

FIG. 3 shows the total 12 hour in vitro production of SCFA in the gut, that is the in vitro production rate of SCFA multiplied by the amount of gut material in the various sections. The data presented here are normalized to production of SCFA pr kg feed.

The data clearly indicate that the addition of D-tagatose to the diet, in a dose response manner promote the microbiological production of butyrate, whereas the total production of acetate is not influenced.

The following abbreviations are used in FIG. 3:

For=formic acid (formate)

Acet=acetic acid (acetate)

Prop=propionic acid (propionate)

I-but=iso-butyric acid (iso-butyratet)

But=butyric acid (butyrate)

I-val=iso-valeric acid (iso-valerate)

Val=valeric acid (valerate)

Cap=capronic (capronate)

Lact=lactic acid (lactate)

Example 3

In this pig study the in vivo absorption of SCFA in the blood is measured by taking blood samples simultaneously from 3 catheters in Vena Mesenterica, Ateria mesenterica and Vena Porta over a 12 hour period after the morning feeding. The absorption is measured in the same 5 pigs at 3 different occasions, that is after 7 days adaptation to standard pig diet+20% sucrose (sucrose), the first day of switching to a standard pig diet+20% D-tagatose (unadapted), and after 7 days adaptation to a standard pig diet+20% D-tagatose (adapted). The concentration of SCFA's is determined in samples from the portal vein, that is the blood stream leading from the digestive system to the liver, and in the arterial blood, that is the blood stream before the digestive system. The difference between the two integrated by time is a measure of the intestinal absorption of SCFA's.

Figure 4:
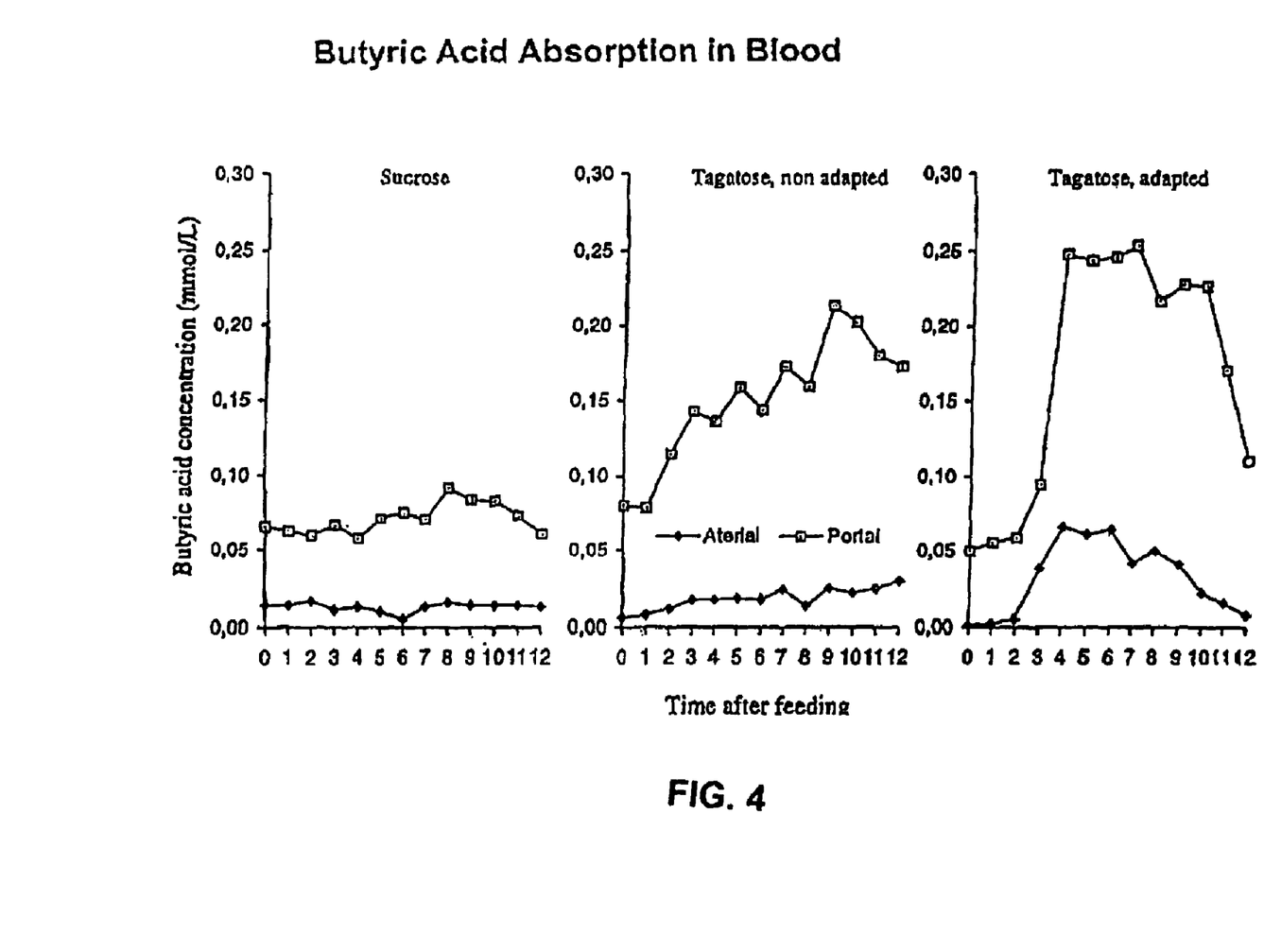
FIG. 4 shows the butyric acid absorption in the blood.

FIG. 4 shows the concentration of butyrate in the portal vein and in the arterial blood as a function of time after feeding. The area between the 2 curves is equal to the total absorption of butyrate from the intestine.

When the pigs were on the 20% sucrose diet, the concentration of butyrate in the portal vein is low and stable over time and very low in the arterial blood, indicating that the absorbed butyrate is cleared by the liver. In the 2. period, unadapted to the 20% D-tagatose diet, the amount of butyrate in the portal vein is gradually increasing over the 12 hours of measuring. When the pigs were measured after 7 days of adaptation to the 20% D-tagatose diet, the concentration of butyrate in the portal blood shows a very steep increase a few hours after feeding, and also the concentration in arterial blood is increasing, indicating that the liver is no longer able to clear the portal vein absorbed butyrate. The total absorption of butyrate represented by the area between the 2 curves does not differ in the adapted and unadapted state.

The absorption of acetate and propionate is not increased by addition of D-tagatose to the diet.

The in vivo absorption of butyrate in the portal vein does not directly reflect the production of butyrate in the colon. Under normal conditions a great part of the produced butyrate is utilized by the colonic mucosa before entering the blood. The very large in vivo absorption of butyrate merely reflects a production of butyrate in the colon that far exceeds the utilisation by the mucosal cells.

These absorption data clearly support a D-tagatose induced production of butyrate in vivo, and that the adaptation to butyrate production takes place within 12 hours.

Example 4

In this study 16 human volunteers deliver a faeces sample before any intake of D-tagatose (unadapted) and another faeces sample after 14 days' intake of 3×10 g of D-tagatose pr day (adapted). The 16 volunteers are on controlled diet 4 days before the delivery of each faeces samples. Faeces slurries, 20%, were incubated at 37° C. and anaerobic conditions for 48 hours with or without 1% D-tagatose added. Samples for determination of SCFA were taken after 4 hours and after 48 hours of incubation. The amount of SCFA produced by D-tagatose is calculated as the amount produced in the assay with 1% D-tagatose added subtracted by the amount produced in the assay without D-tagatose. Further, the delivered faeces samples were tested for content of various intestinal bacteria counts by spreading on selective media.

Table 2 shows the mol % of the various SCFA produced in vitro by D-tagatose in the unadapted and adapted state, and also the actually produced total SCFA in mmol pr 1 of incubation slurry.

TABLE 2

In Vitro Fermentation of Tagatose by Incubation of Human Faeces Molar Ratios (Mole %) of SCFA's

| | 4 hours of incubation | | 48 hours of incubation | |
| --- | --- | --- | --- | --- |
| | Non-adapted | Adapted | Non-adapted | Adapted |
| Formic acid | 0.5 | 5.8 | 0.0 | 0.1 |
| Acetic acid | 62.8 | 42.1 | 37.7 | 35.3 |
| Propionic acid | 0.0 | 4.1 | 0.0 | 0.5 |
| Butyric acid | 24.5 | 34.7 | 38.7 | 47.0 |
| Valeric acid | 3.0 | 1.0 | 1.2 | 1.6 |
| Capronic acid | 6.7 | 3.5 | 15.2 | 13.5 |
| Heptanic acid | 1.1 | 0.6 | 1.6 | 1.2 |
| Lactic acid | 3.9 | 9.0 | 8.6 | 3.0 |
| Total | 100.0 | 100.0 | 100.0 | 100.0 |
| Total SCFA (production mmol/l) | 8.8 | 24.3 | 49.0 | 44.0 |

The production of SCFA is 8.8 mmol/l and 24.3 mmol/l after 4 hours of incubation in the unadapted and adapted state, respectively. The ratio of butyrate after 4 hours of incubation is also higher in the adapted state and much higher than the normally observed 15–20%. After 48 hours of incubation there is no longer any difference in the amount of SCFA produced, and the proportion of butyrate is high both in the adapted and unadapted incubations. These data also support a D-tagatose induced production of butyrate, and an adaptation in the in vitro incubation system within 48 hours.

Figure 5:
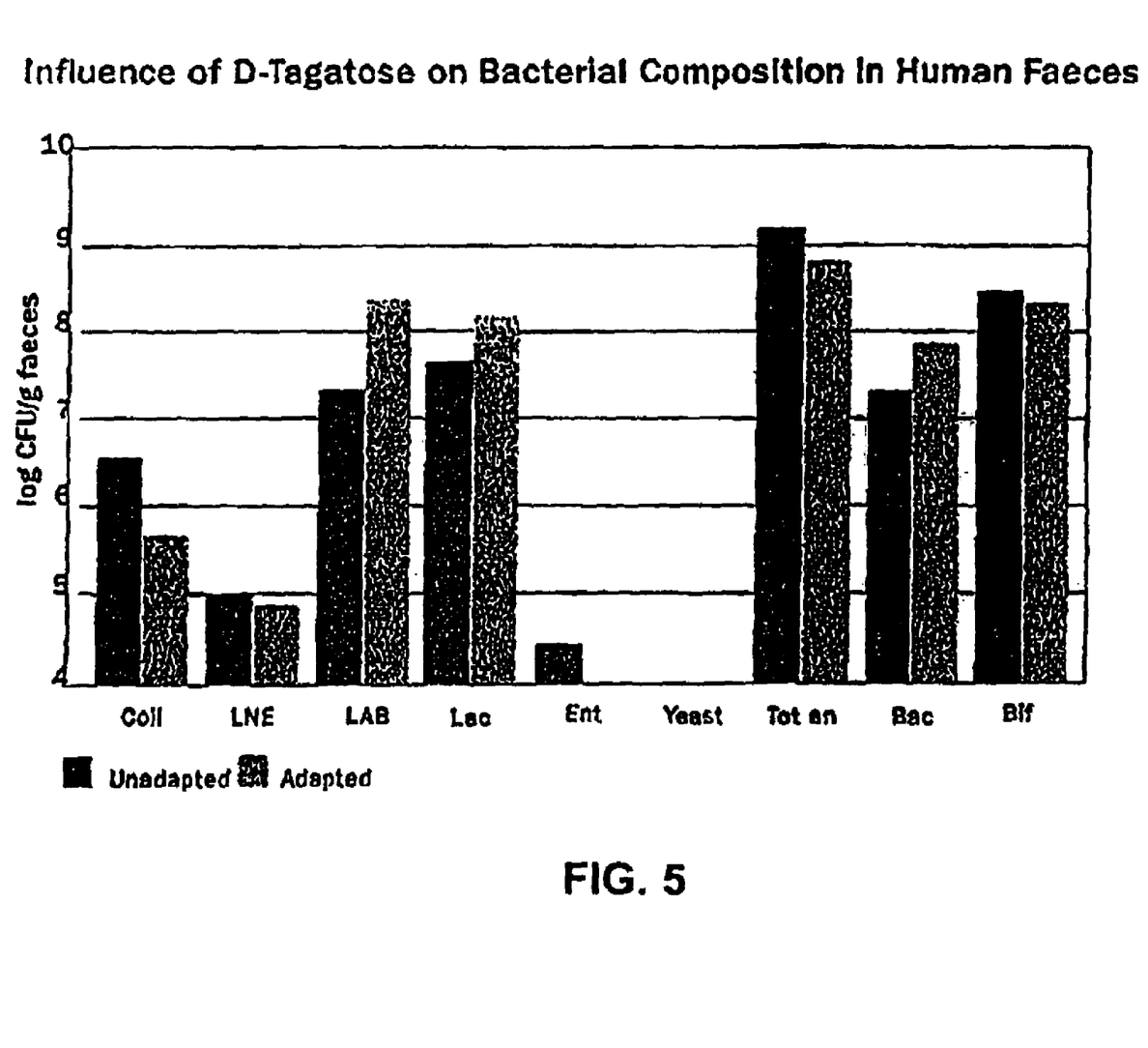
FIG. 5 shows the influence of D-tagatose on bacterial composition in human faeces.

FIG. 5 shows the results of counting bacteria (log scale) on different selective media. The number of lactobacilli and lactic acid bacteria is increased in number, and enterobacteria is decreased in feaces of human volunteers ingesting D-tagatose for 14 days compared to the same persons not ingesting D-tagatose.

The following abbreviations are used in FIG. 5:

coli=coliform bacteria

LNE=lactose neg. enterobacteria

LAB=lactic acid bacteria

LAC=lactobacilli

Ent=enterococci

Tot an=anaerobes

Bac=bacteroides

Bif=bifidobacteria

CONCLUSION

The 2 in vitro studies in pigs (Examples 1 and 2) with addition of D-tagatose and relying on D-tagatose escaping absorption in the small intestine, showed a D-tagatose induced butyrate production. More importantly, the concentration in the colon of pigs immediately after slaughter, reflecting the concentrations in vivo, showed a dose response increase in butyrate concentration to the amount of D-tagatose ingested. Even more importantly, the in vivo absorption of butyrate in the portal vein documents a very prominent butyrate inducing effect of D-tagatose.

None of these above mentioned studies in pigs, that is taking of samples of colon content and blood samples from the portal vein, can be performed in humans for ethical reasons. However, pig and human have the same structure of the gastrointestinal tract and harbors qualitatively the same types of intestinal bacteria, so the pig serves as a good model for humans in digestion and fermentation. To perform human studies, one has to rely on in vitro studies with D-tagatose added to human faecal slurries. These studies showed the same trends of D-tagatose induced butyrate production as in the pig incubations performed with colon content slurries.

The intestine of both pig and human harbors bacteria which have butyrate as the fermentation end product. D-tagatose is a rather rare sugar for intestinal bacteria and is only fermented by a limited number of genera of bacteria, enterococci, lactobacilli, and obviously some butyrate producing intestinal bacteria. Other fibres or undigested carbohydrates are either not a substrate for butyrate producing bacteria, or competition for the delivered substrate favours growth of other bacteria. A reasonable explanation for the butyrate inducing effect of D-tagatose is that butyrate producing bacteria is favoured over most other bacteria when supplying D-tagatose. The adaptation seen with ingestion of D-tagatose in both pigs and human volunteers is probably due to selection of butyrate producing bacteria in the colon. The in vivo absorption study in pigs showed that the adaptation or selection of bacteria takes place already within 12 hours. Similarly, the in vitro study with human faeces indicates selection of bacteria within the 48 hours of incubation.

Overall, between 10 and 60 g of carbohydrate containing compounds become available to the human flora on a daily basis and constitute the major influence on intraluminal events (G. T. Mcfarlane and J. H. Cummings 1991. The colonic flora, fermentation, and large bowel digestive function; In The large intestine: Physiology, pathophysiology, and disease, Ed: S. F. Phillips, J. H. Pemberton and R. G. Shorter. Raven Press, Ltd., New York.). The intake of D-tagatose is, like all other unabsorbable carbohydrates, in practice limited in intake by gastrointestinal side effects.

Oral intake 5–30 g of D-tagatose pr day aiming at a pre-biotic effect is very easily achieved as D-tagatose can be incorporated in almost any food, but most obviously in applications as a substitute for sucrose, for example, as mentioned, in confectionery and chewing gum, ice cream and other desserts, yoghurts, cereals and energy bars, soft drinks and health drinks

We claim:

1. A method for selectively inducing production of butyrate by bacteria in the colon of a human in need thereof comprising administering D-tagatose to said human in a daily amount of 5–30 grams to selectively induce production of butyrate.

2. A method according to claim 1 wherein D-tagatose is administered orally.

3. A method according to claim 1 wherein the daily amount is 5–15 grams.

4. A method according to claim 2 wherein D-tagatose is administered orally in a food product.

5. A method according to claim 4 wherein the food product is selected from a confectionery, chewing gum, ice cream, desert, soft drink, breakfast cereal, yogurt, health drink and health bar.

6. A method for selectively stimulating growth of lactobacilli and lactic acid bacteria in the colon of a human in need thereof comprising administering D-tagatose to a human in a daily amount of 5–30 grams to selectively stimulate growth of lactobacilli and lactic bacteria in the colon.

7. A method according to claim 6 wherein D-tagatose is administered orally.

8. A method according to claim 7 wherein D-tagatose is administered orally in a food product.

9. A method according to claim 8 wherein the food product is selected from a confectionery, chewing gum, ice cream, dessert, soft drink, breakfast cereal, yogurt, health drink and health bar.

10. A method according to claim 6 wherein the daily amount is 5–15 grams.

* * * * *